United States Patent [19]

Fu et al.

[11] Patent Number: 4,659,853
[45] Date of Patent: Apr. 21, 1987

[54] PROCESS FOR THE PRODUCTION OF ISOTHIOCYANATE DERIVATIVES

[75] Inventors: Yun-Lung Fu, New Haven; Peter J. Strydom, Fairfield, both of Conn.

[73] Assignee: American Cyanamid Company, Stamford, Conn.

[21] Appl. No.: 821,297

[22] Filed: Jan. 22, 1986

[51] Int. Cl.$^4$ .................. C07C 155/02; C07C 155/08
[52] U.S. Cl. ..................................... 558/19; 558/233; 560/148
[58] Field of Search ................... 558/233, 19; 560/148

[56] References Cited

U.S. PATENT DOCUMENTS 4,482,500 11/1984 Lewellyn .............................. 558/17

Primary Examiner—John M. Ford
Assistant Examiner—Robert C. Whittenbaugh
Attorney, Agent, or Firm—Frank M. Van Riet

[57] ABSTRACT

Derivatives of alkoxy, aryloxy and alkene isothiocyanates are produced by the reaction of a haloformate, an alkali, alkaline earth metal, lead or ammonium thiocyanate and a compound having the formula $R^1YH$ wherein $R^1$ is alkyl, aryl or alkoxy, Y is oxygen, sulfur or $NR^2$ and $R^2$ is hydrogen or $R^1$, in the presence of a solvent or water and a catalyst.

10 Claims, No Drawings

PROCESS FOR THE PRODUCTION OF ISOTHIOCYANATE DERIVATIVES

BACKGROUND OF THE INVENTION

Many thionocarbamate, thiourea and dithiocarbamate derivatives of carbonyl isothiocyanates are well known in the art, as are methods for their production. The most prevalent methods comprise the formation of the carbonyl isothiocyanate, the recovery and purification thereof and the final reaction thereof with the appropriate coreactant to produce the desired derivative. Prior processes however, result in yields of the carbonyl isothiocyanates of only 30–60% of theoretical. Thus, the need for recovery and purification of the carbonyl isothiocyanate and the relatively poor yields seriously detract from the commercial production of derivatives of these carbonyl isothiocyanates to the extent that they are very expensive to purchase or produce if such are commercially attainable at all.

Accordingly, if a process could be developed wherein the thionocarbamate, thiourea and dithiocarbamate derivatives of carbonyl isothiocyanates could be produced more cheaply at high yields and purity, a long felt need in the art would be satisfied.

SUMMARY OF THE INVENTION

A procedure for the formation of derivatives of alkoxy, aryloxy and alkene isothiocyanates has now been devised whereby the desired derivatives are obtained in higher yields and purity than when prior art techniques are employed. The process of the present invention eliminates the need to isolate the isothiocyanate and provides a simple, one-pot process of commercial importance.

DESCRIPTION OF THE INVENTION INCLUDING PREFERRED EMBODIMENTS

The present invention relates to a process for the production of carbonyl isothiocyanate derivatives which comprises:

(1) reacting a compound having the formula

 (I)

wherein R is a $C_1$–$C_8$ alkyl radical, a $C_3$–$C_4$ alkene radical or a $C_6$–$C_{10}$ aryl radical and X is a halogen atom, with a compound having the formula

MSCN    (II)

wherein M is an alkali or alkaline earth metal, lead or $NH_4$ and a compound having the formula $R^1YH$    (III)

wherein $R^1$ is a $C_1$–$C_{10}$ alkyl radical, a $C_6$–$C_{10}$ aryl radical or a $C_1$–$C_8$ alkoxy radical and Y is oxygen, sulfur or $NR^2$, wherein $R^2$ is hydrogen or $R^1$, in the presence of either (A) a solvent for the compounds or (B) water and a catalyst, provided that when Y is oxygen or sulfur the solvent can be an excess of the compound of Formula (III), at a temperature ranging from about $-10°$ C. to about 120° C. and for up to about 16 hours and (2) recovering the resultant product.

The reaction proceeds according to the equation:

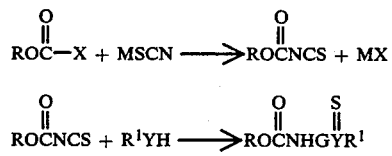

wherein R, M, $R^1$ and Y are as expressed above.

The process of the present invention proceeds cleanly via a one-pot i.e., one-kettle, reaction wherein the intermediate compound,

need not be isolated before reaction thereof with the compound $R^1YH$ can be achieved.

The reaction proceeds readily at a temperature ranging from about $-10°$ C. to about 120° C., preferably from about 10° C. to about 90° C. for up to about 16 hours, preferably from about 1 to about 6 hours, when an organic solvent is used and about $-10°$ to 40° C., preferably about 5°–15° C., when an aqueous system is used.

When an organic solvent is employed, any organic compound which is a solvent for the compounds undergoing reaction may be used. Suitable solvents include alcohols such as methanol, ethanol, butanol, etc; nitriles such as acetonitrile, etc., aromatic compounds such as benzene, toluene, xylene etc., halogenated hydrocarbons such as carbon tetrachloride; dimethylsulfoxide; tetrahydrofuran; ketones such as acetone etc. When an organic solvent is used, it is preferably used alone, however, it may be used in conjunction with a catalyst such as hydrochloric acid, dibutyltin dilaurate and the like.

When water is used, it must be used in conjunction with from about 0.1% to about 10.0%, by weight, based on the weight of the compound of Formula (1), of a catalyst comprising a six-membered mononuclear or ten-membered, fused, polynuclear, aromatic, heterocyclic compound having 1 or 2 nitrogen atoms as the only hetero atoms in the ring, as disclosed in U.S. application Ser. No. 821,302 filed concurrently herewith. Such catalysts include pyridine, quinoline, pyrimidine, pyrazine, quinoxaline and the like and substituted derivatives thereof such as their alkyl, halo, nitrile alkoxy, etc. derivatives. Any derivative may be used except those substituted in the 2-position.

As mentioned briefly above, when Y is oxygen or sulfur, the solvent for the reaction may be the $R^1YH$ compound of Formula III used in an excess of that required to enter into the reaction. The use of the Formula III compound as a solvent is possible because the reaction of said compound with the reaction product of the compounds of Formulae I and II is slow as compared to the coreaction of the compounds of Formulae I and II. Accordingly, the Formulae I and II compounds are able to coreact while the Formula III compound is only reacting with the reaction product of the Formulae I and II compounds. When Y is $NR^2$, however, the Formula III compound reacts rapidly with the Formula I compound and competes with the reaction between the compounds of Formulae I and II and therefore cannot function effectively as a solvent.

A preferred solvent, preferred in that it has been found to result in very high yields of product in very high purity, is a mixture of 50% to 85% of toluene and 15% to 50% of acetonitrile.

Examples of compounds falling within the scope of those represented by Formula I, include, methylchloroformate, ethylchloroformate, propylchloroformate, butylchloroformates, amylchloroformates, hexylchloroformates, octylchloroformates, butenechloroformate, benzylchloroformate, phenylchloroformate, naphthylchloroformate, etc. and their corresponding bromo, iodo or fluoro derivatives.

Alkali and alkaline earth thiocyanates corresponding to Formula II, include, sodium, lithium, potassium, rubidium, cesium, beryllium, magnesium, calcium, strontium and barium thiocyanates. Lead thiocyanate and ammonium thiocyanate can also be used.

While it is possible, and oftimes preferable, to conduct the reaction of the compounds of Formulae I, II and III by adding all three compounds to the reaction vessel ab initio, it is more often preferred to allow the reaction of the compounds of Formulae I and II to proceed to substantial completion before adding the compound of Formula III. Such a procedure is even more preferred when the reaction is conducted using a water-catalyst system. However, recovery and purification of the reaction product of the Formulae I and II compounds is not necessary.

The reaction can be monitored in any event by testing for the disappearance of the compound of Formula I using, for example, gas chromatography. When the test sample shows less than about 1% of the Formula I compound, the Formula III compound is added, preferably slowly so as to maintain the temperature within the desired range and to prevent a run-away reaction. The addition may be conducted with cooling.

When either an aqueous system or an organic solvent system is used, the reaction can be monitored for production of the final product, again using gas chromatography. A phase separation occurs and the resultant aqueous layer is discarded. The desired final product is recovered by vacuum distillation to remove water and impurities.

Suitable compounds represented by Formula III include alcohols such as methanol, ethanol, n-propyl alcohol, isopropyl alcohol, n-butyl alcohol, isobutyl alcohol, sec-butyl alcohol, amyl alcohols, hexyl alcohols, heptyl alcohols, cyclopentyl alcohol, cyclohexyl alcohol, allyl alcohol, benzyl alcohol, etc; amines such as methylamine, ethylamine, hexylamine, isopropylamine, isobutylamine, amylamines, cyclohexylamine, octylamine, benzylamine, etc; mercaptans such as methyl mercaptan, ethyl mercaptan, propyl mercaptan, butyl mercaptans, amyl mercaptans, hexyl mercaptans, benzyl mercaptan, allyl mercaptan, and the like.

The following examples are set forth for purposes of illustration only and are not to be construed as limitations on the present invention except as set forth in the appended claims. All parts and percentages are by weight unless otherwise specified.

EXAMPLE I

To a suitable reaction vessel equipped with a condenser and a motor-driven stirrer, are added 405 parts of water. Crushed sodium cyanide (245 parts, 5 moles) is then added with stirring. To the sodium cyanide solution is introduced 4.6 parts of a 40% ethanolic solution of mixed $C_8$-$C_{10}$ dialkyldimethyl ammonium chlorides. With intermittent ice-water cooling, sulfur (160 parts, 5 moles) is added in small portions in about ½ hour. Temperature is kept at 40°-50° C. during the sulfur addition. As the exotherm subsides, heat is applied to heat the reaction mixture to 95° C. and held at that temperature for one hour. The sodium thiocyanate concentration on cooling is analyzed to 49.8% vs. 50% theoretical.

The sodium thiocyanate solution is further cooled to 0° C. with a ice/methanol cooling bath. With continuing stirring, ethylchloroformate (542.5 parts, 5 moles) is added in a thin stream. The temperature rises to 5° and is cooled back to −2° C. Pyridine (14.67 parts) is added to the reaction mixture dropwise in about 10 minutes. The reaction temperature is allowed to rise slowly to 8°-10° C. Reaction is continued at this temperature until all ethylchloroformate is reacted. This is monitored by withdrawing samples of the organic layer hourly and injecting into a gas chromatographic machine. At the end of about 4 hours, the GC shows essentially no traces of ethylchloroformate and the area percent for ethoxycarbonyl isothiocyanate is nearly 90%. Only a slight trace of ethoxycarbonyl thiocyanate (<3%) is detected by GC.

The pyridine catalyst is then carefully neutralized with 10% hydrochloric acid (67.8 parts). Water (450 parts) is added to dissolve the by-product sodium chloride salt (10-15 mins.). Temperature is cooled to 5° C. and a first portion of isobutyl alcohol (185 parts) is added. After stirring five minutes, the agitator is stopped and the reaction mixture quickly separates into two layers. The bottom aqueous layer is drawn off with a suction tube. Agitation is resumed. The balance of isobutyl alcohol is introduced (555 parts, total isobutyl alcohol: 740 parts, 10 moles). The temperature is allowed to rise slowly to 20°-25° C. The reaction is continued at this temperature range for four and half hours at which time the isothiocyanate is essentially reacted. The reaction mixture is then vacuum stripped under mild heat (45° C. and 125 mm Hg) for 1½ hours. The finished product contains 76% of the desired product N-ethoxycarbonyl-O-isobutyl thionocarbamate. The balance is mainly isobutyl alcohol and a small trace of diethyl carbonate. The yield is 1,221 parts or 90.6% of theoretical (1,348 parts based on 76% purity). For mining reagent application, the product is quite suitable without further purification. However, the product mixture is subjected to further vacuum distillation (60° C. and 20 mm Hg). The pure product yield is 85% (870 parts vs. 1025 parts theoretical), which analyzes correctly by IR and NMR determinations.

EXAMPLE 2

The procedure given in Example 1 is followed essentially step by step except that quinoline is used to replace pyridine as the catalyst. The yield of the product is 1,295 parts vs. 1,348 parts of 76% purity, of 96% theoretical.

EXAMPLE 3

In a suitable reaction vessel equipped with a condenser and a mechanically driven stirrer, a 50% solution of NaSCN in water (162 parts) is prepared as shown in Example I. Pyridine (4 mls) and ethyl chloroformate (108.5 parts) are introduced to the flask in the same manner as given in Example I. The ethoxycarbonyl isothiocyanate formation is completed in 4½ hours at 8°-10° C. as determined by GC. The pyridine catalyst is neutralized with 10% HCl (18.1 parts). Water (100 parts) is then added to dissolve NaCl salt. Toluene (50 ml) is introduced to the reaction mixture. n-Butylamine (73 parts) is added dropwise at a temperature range of 5°–10° C. The reaction is continued at 20°–25° C. for two hours at which time the ethoxycarbonyl isothiocyanate is essentially all reacted as determined by GC. The agitation is stopped and the top organic layer is separated from the aqueous salt layer. The crude product, ethoxycarbonyl-N-n-butyl thiourea comprises 241 parts vs. 247 parts theoretical or 97.5%. Purity of the product is determined by comparison with an authentic sample of ethoxycarbonyl-N-n-butyl thiourea prepared separately. GC analysis shows a purity of 81.9% vs. 82.6% theoretical. The main impurity in the product is toluene which is vacuum distilled off. However, as a mining reagent it is rather convenient to apply the product in a solution form. In separate experiments, it is shown that neutralization of the pyridine catalyst is not necessary and that organic solvents such as heptane, xylene or ethyl acetate can be used instead of toluene.

EXAMPLE 4

Into a mixture of 16.2 parts (0.2 mole) of sodium thiocyanate, 20 ml of toluene, and 0.5 ml of pyridine are added 19.6 parts (0.18 mole) of ethyl chloroformate dropwise. An exotherm results, raising the temperature to 50° C. After the addition, the mixture is heated at 50°–55° C. for 2 hours, at which time g.c. analysis shows 95% completion. The reaction mixture is cooled to room temperature and 13.3 parts (0.18 mole) of isobutyl alcohol are added. The mixture is heated at 50° C. for 2 hours, at which time G.C. analysis shows 90% completion. The mixture is cooled to room temperature and 30 ml of water are added to dissolve the sodium chloride by-product. The water layer is separated and extracted with a small amount of toluene. The toluene is removed by vacuum distillation (60°–65° C. at 25 in. Hg vacuum and nitrogen purge). The yield of N-ethoxycarbonyl-O-isobutylthionocarbamate after stripping, is 28.4 parts (77%) with a purity of 90% by g.c.

EXAMPLE 5

To 81 parts of an aqueous 50% NaSCN solution are added 2.0 parts of quinoline. With stirring, the mixture is cooled to 8° C. with ice/water. Phenylchloroformate (78.3 parts) is introduced dropwise in 1½ hours. The reaction is essentially complete in about 1¾ hours at 10° C. as monitored by GC. To the product, phenoxycarbonyl isothiocyanate, are added 40 parts of isobutanol dropwise (30 mins). After reacting one hour of 10° C., water (180 mls) is added to dissolve the salt. Toluene is added to facilitate the phase separation. The organic layer is vacuum stripped to give a low melting solid product (108.7 parts or 85.8% yield) which has the correct IR analysis for N-phenoxycarbonyl-O-isobutyl thionocarbamate.

EXAMPLE 6

A 50% aqueous solution NaSCN (81 parts), containing 2 parts of quinoline, is chilled to 10° C. Allylchloroformate (60.3 parts) is added dropwise in ½ hour. The reaction is monitored by GC. After 2 hours at 10° C., the conversion to alloxycarbonyl isothiocyanate is only 40%. The temperature is raised to 20° C. and held for two hours after which time the allylchloroformate has all reacted. The conversion is 89%. Isobutyl alcohol, 73 parts, is then added and the reaction continued for three hours at 25° C. Water (50 parts) is added and the by product salt and and the organic layer is evaporated. After vacuum stripping off the excess isobutanol, the final liquid product (124 parts) gives the correct IR and NMR analysis for N-alloxycarbonyl-O-isobutyl thionocarbamate.

EXAMPLE 7

Ethoxycarbonyl isothiocyanate is prepared by reacting 162 parts of an aqueous 50% NaSCN and 108.5 parts of ethylchloroformate in the presence of 4.0 parts of quinoline catalyst under conditions similar to those given in Example 1. After 7 hours at 10° C., the GC shows that ethylchloroformate has all reacted. Isobutyl alcohol (142 parts) is added to the reaction mixture and the temperature is kept at 15°–20° C. After 3½ hours of reaction, 100 parts of water are added to dissolve the salt. The organic layer is separated and the excess isobutyl alcohol (45° C. and 25″ Hg) is vacuum stripped off. The final product (190 parts or 92.6% yields) gives the correct IR and NMR analysis for N-ethoxycarbonyl-O-isobutyl thionocarbamate.

EXAMPLE 8

Ethoxycarbonyl isothiocyanate is prepared in a similar manner as given in Example 7. The reaction mixture is cooled to 0° C. Water (100 parts) is added to dissolve the salt. N-Butylamine (73.14 parts) is added dropwise over one hour while the temperature is kept at 5°–8° C. Isobutyl alcohol (51 parts) is added to the thickened mixture. After stirring for two hours at room temperature, the organic layer is separated. The isobutyl alcohol is vacuum stripped off. The solid product (184 parts) has the correct IR and NMR analysis for N-ethoxycarbonyl-N'-n-butyl thiourea.

EXAMPLE 9

In suitable three necked vessel, ethoxycarbonyl isothiocyanate is prepared by reacting 648 parts of an aqueous 50% NaSCN with 440 parts of ethylchloroformate in the presence of 16 parts of quinoline under similar conditions as given in Example 7. The reaction mixture is cooled to 0° and 400 parts of water are added to dissolve the salt. Isopropylamine (118 parts) and n-butylamine (146 parts) are added dropwise at 5° C. over 2½ hours. Isobutyl alcohol (197 parts) is added to the reaction mixture. After stirring two hours at room temperature, the organic layer is separated and vacuum stripped. The viscous oily product (730 parts) gives the correct IR and NMR analysis for a mixture of N-ethoxycarbonyl-N'-isopropyl thiourea and N-ethoxycarbonyl-N'-n-butyl thiourea.

EXAMPLE 10

Following the procedure of Example 1, to 49 parts of the ethoxycarbonyl isothiocyanate in 87 parts of ethylacetate are added 30 parts of isobutyl mercaptan. The reaction mixture is heated to 45° C. and held for 4 hours. The ethyl acetate solvent is vacuum stripped off to give 71 parts of N-ethoxycarbonyl-S-isobutyl dithiocarbamate with correct IR and NMR analysis.

EXAMPLE 11

Again following the procedure of Example 1, to 1.31 parts of the ethoxycarbonyl isothiocyanate in 6 parts of methylene chloride are added 1.31 parts of butoxypropylamine. After 2 hours at room temperature, the methylene chloride is evaporated off. The viscous liquid product N-ethoxycarbonyl-N'-n-butoxypropyl thiourea (2.6 parts) gives the correct IR analysis.

EXAMPLES 12 AND 13

Following the procedure of Example 10, 13.1 parts of ethoxycarbonyl isothiocyanate are reacted with 9.0 parts of n-amyl alcohol at room temperature for 4 hours. N-ethoxycarbonyl-O-n-amyl thionocarbamate (22 parts) is obtained with correct IR analysis. Similarly, 13.1 parts ethoxycarbonyl isothiocyanate is reacted with 10.2 parts of hexyl alcohol. 23 Parts of semi-solid product N-ethoxycarbonyl-O-n-hexyl thionocarbamate, are obtained with correct IR analysis.

EXAMPLE 14

The procedure of Example 1 is again followed except that potassium thiocyanate solution (50%) is used. Similar results are obtained.

EXAMPLE 15

Again following the procedure of Example 1, sodium thiocyanate solution is reacted with 2-ethylhexylchloroformate. The reaction is complete after six hours at 10° C. Excellent results are obtained.

EXAMPLE 16

Following the procedure of Example 15, n-octylchloroformate is used in place of the 2-ethylhexylchloroformate, all else remaining equal. An excellent yield of product is recovered.

EXAMPLE 17

Again following the procedure of Example 15 except that ethylbromoformate is employed, similar results are achieved.

EXAMPLE 18

To a suitable three-necked reaction vessel equipped with a condenser and a mechanical stirrer are charged 316 parts of anhydrous methanol and 260 parts of toluene. To the solvent mixture are added 196 parts of crushed sodium cyanide. With stirring, sulfur powder (128 parts) is introduced in small portions. After the exotherm subsides, the reaction mixture is heated to reflux (74° C.) After refluxing for one hour, an additional 607 parts of toluene are added to azeotrope off the methanol. Total distillate volume is about 605 parts. Acetonitrile (240 parts) and toluene (130 parts) are charged to the reaction mixture. After heating to 80° C., 390.4 parts of ethylchloroformate are carefully added through an addition funnel over ½ hour. The reaction is continued at 80°-85° for one hour and 40 minutes until all ethylchloroformate is reacted as monitored by GC. The reaction mixture is then cooled to 0° C. A mixture of 132 parts of isobutylamine and 106 parts of isopropylamine is then carefully added in about one hour and while maintaining the temperature at 10°-15° C. with ice/water cooling. After the addition of the amines, the reaction temperature is allowed to rise to room temperature and held for two hours at which time all ethoxycarbonyl isothiocyanate is reacted as monitored by GC. Water (600 parts) is added to dissolve the by-product sodium chloride. The aqueous bottom layer is separated from the top organic layer using a separating funnel. The crude product is then vacuum stripped at 45° C. The product, a mixture of N-ethoxycarbonyl-N'-isobutyl thiourea and N-ethoxycarbonyl-N'-isopropyl thiourea, (620 parts or 87.3%) assays 97% purity by GC.

EXAMPLE 19

Following the procedure of Example 18, N-ethoxycarbonyl-O-isobutyl thiocarbamate is prepared in a similar manner. The sodium thiocyanate is formed by the reaction of sulfur with sodium cyanide in methanol/toluene solvent. After azeotroping off methanol with toluene, ethylchloroformate is added to form the ethoxycarbonyl isothiocyanate. To the resultant reaction mixture are added 275 parts of isobutanol at 75° C. in 20 minutes. The reaction is continued at 80° C. for ½ to one hour until all the isothiocyanate is reacted as monitored by G.C. After cooling to room temperature, water 600 parts is added to dissolve the salt. The organic product layer is separated from the aqueous layer. The crude product is then vacuum stripped at 45° C. to give a 598 parts or 78% yield with 90% purity by GC analysis.

EXAMPLE 20

N-ethoxycarbonyl-S-isobutyl dithiocarbamate is prepared by reacting the ethoxycarbonyl isothio cyanate intermediate with isobutyl mercaptan following the procedures of Example 18. Thus, in place of the isopropyl and isobutyl amines, 320 parts of isobutyl mercaptan are added at 60° C. in ½ hour. The reaction is continued at 65°-70° C. for 3 hours or until all the isothiocyanate is reacted as determined by G.C. The resultant reaction mixture is cooled to room temperature and water (600 parts) is added to dissolve the salt. The organic layer is separated from the aqueous layer and vacuum stripped to give 600 parts of the product (71% yield) with 90% purity.

We claim:

1. A process for the production of thionocarbamate, thiourea and dithiocarbamate derivatives of a carbonyl isothiocyanate which comprises:

(1) reacting a compound having the formula:

wherein R is a $C_1$-$C_8$ alkyl radical, a $C_3$-$C_4$ alkene radical or a $C_6$-$C_{10}$ aryl radical and X is a halogen atom, with a compound having the formula:

wherein M is an alkali or alkaline earth metal, lead or $NH_4$ and a compound having the formula:

wherein $R^1$ is a $C_1$-$C_{10}$ alkyl radical, a $C_6$-$C_{10}$ aryl radical or a $C_1$-$C_8$ alkoxy radical and Y is oxygen, sulfur or $NR^2$, wherein $R^2$ is hydrogen or $R^1$, in the presence of (A) a solvent for the compounds or (B) water and a catalyst comprising a six-membered mononuclear or ten-membered, fused, polynuclear, aromatic heterocyclic compound having 1 or 2 nitrogen atoms as the only hetero atoms in the ring, and provided that when Y is oxygen or sulfur the solvent can be an excess of the compound of Formula (III), at a temperature ranging from about −10° C. to about 120° C. for up to about 16 hours and (2) recovering the resultant derivative.

2. A process according to claim 1 wherein the compound of Formula (III) is added to the reaction vessel after the reaction between the compounds of Formulae (I) and (II) is substantially complete.

3. A process according to claim 1 wherein R is ethyl, $R^1$ is butyl and Y is oxygen.

4. A process according to claim 1 wherein R is ethyl, $R^1$ is isopropyl, Y is $NR^2$ and $R^2$ is hydrogen.

5. A process according to claim 1 wherein R is phenyl.

6. A process according to claim 1 wherein R is allyl.

7. A process according to claim 1 wherein $R^1$ is isobutyl, Y is $NR^2$ and $R^2$ is hydrogen.

8. A process according to claim 1 wherein water and pyridine are used as the reaction media and catalyst.

9. A process according to claim 1 wherein water and quinoline are used as the reaction media and catalyst.

10. A process according to claim 1 wherein said solvent is a mixture of toluene and acetonitrile.

* * * * *